United States Patent [19]

Chang et al.

[11] Patent Number: 5,789,170
[45] Date of Patent: Aug. 4, 1998

[54] SPECIFIC CO-ACTIVATOR FOR HUMAN ANDROGEN RECEPTOR

[75] Inventors: Chawnshang Chang, Pittsford, N.Y.; Shuyuan Yeh, Madison, Wis.

[73] Assignee: Wisconsin Alumni Research Foundation, Madison, Wis.

[21] Appl. No.: 652,207

[22] Filed: May 23, 1996

[51] Int. Cl.$^6$ .............................. C12Q 1/68; C12N 5/10; C12N 15/79

[52] U.S. Cl. .................... 435/6; 435/320.1; 435/366

[58] Field of Search ................. 435/6, 320.1, 325, 435/366; 536/23.1, 23.5

[56] References Cited

PUBLICATIONS

Chang, Chawnshang, et al., "Structural analysis of complementary DNA and amino acid sequences of human and rat androgen receptors," *Proc. Natl. Acad. Sci. USA*, 85:7211–7215 (Oct. 1988).

Santoro, Massimo, et al., "Molecular characterization of RET/PTC3; a novel rearranged version of the RETproto-oncogene in a human thyroid papillary carcinoma," *Activation of RET/PTC3 in Thyroid Carcinomas*, pp. 509–516 (Sep. 14, 1993).

Yeh, Shuyuan, et al., "Cloning and Characterization of a Specific Coactivator, ARA$_{70}$, for the Androgen Receptor in Human Prostate Cells," *Proc. Natl. Acad. Sci. USA*, 93:5517–521 (May 1996).

Young, Win-jing, et al., "Quantitation of androgen receptor mRNA by competitive reverse transcription–polymerase chain reaction," *Endocrine Journal*, 2:321–329 (1994).

*Primary Examiner*—George C. Elliott
*Assistant Examiner*—Robert Schwartzman
*Attorney, Agent, or Firm*—Quarles & Brady

[57] ABSTRACT

A ligand dependent co-activator for the human androgen receptor has been identified. The co-activator, named here ARA$_{70}$, potentiates interaction between androgens and the receptor. The co-activator is useful as a tool in monitoring the androgenic/antiandrogenic effects of possible pharmaceuticals as well as environmental samples. The cDNA for co-activator has been cloned and sequenced.

12 Claims, 1 Drawing Sheet

SPECIFIC CO-ACTIVATOR FOR HUMAN ANDROGEN RECEPTOR

FIELD OF THE INVENTION

The present invention relates to a cloned gene for a protein which co-activates an important hormonal receptor in humans and relates, in addition, to the use of the co-activator protein as an important constituent in clinical tests for diagnoses of human clinical conditions.

BACKGROUND OF THE INVENTION

The class of compounds known as androgens are the hormonal signals responsible for maleness in mammals in general and human beings in particular. As with most hormonal signals, androgens interact with their targets by binding to a receptor, known as the androgen receptor. Recognition of androgens by the androgen receptor initiates a series of transcriptional events giving rise to male-associated processes in certain tissues and organs. The binding of androgens to the androgen receptor is also important in many androgen related diseases and conditions, such as baldness and acne, as well as important clinical diseases such as prostate cancer. The androgen receptor belongs to the steroid receptor super family that plays an important role in male sexual differentiation and prostate cell proliferation. Mutations or abnormal expressions of the androgen receptor in prostate cells may play an important role in the progression of prostate cancer.

When bound to androgens and androgen responsive elements, the androgen receptor can up-regulate or down-regulate the expression of androgen target genes through a complicated process that may involve multiple adaptors or co-activators. Adler et al., *Proc. Natl. Acad. Sci. USA* 89, 6319–6325 (1992). A fundamental issue in the field of steroid hormone regulation is the question or how specific androgen-activated transcription can be achieved in vivo when several different receptors recognize the same DNA sequence. For example, the androgen receptor (AR), the glucocorticoid receptor (GR) and the progesterone receptor (PR) all recognize the same sequence but activate different transcription activities. It has been speculated by some that accessory factors may selectively interact with the androgen receptor to determine the specificity of the androgen receptor target gene activation.

One of the uses for the androgen receptor is to detect the androgenic or anti-androgenic effects of specific candidate human pharmaceutical molecules. The androgenic effect of pharmaceuticals is usually an attribute of potential candidate therapeutic medicines that must be evaluated during the process of total evaluation of a molecule for human therapeutic value. Accordingly, the androgen receptor is used in screens to determine the frequency and specificity by which specific molecules bind to such receptors.

SUMMARY OF THE INVENTION

The present invention is summarized in that a specific co-activator for the human androgen receptor has been isolated and the gene for that co-activator has been cloned sequenced and is presented below.

The present invention is also summarized in that the cloning and reproduction of the androgen receptor activator gene permits new laboratory tests to be made to test the androgen specificity of candidate therapeutic molecules.

Other objects, advantages, and features of the present invention will become apparent from the following specification.

DESCRIPTION OF THE INVENTION

Figure 1:
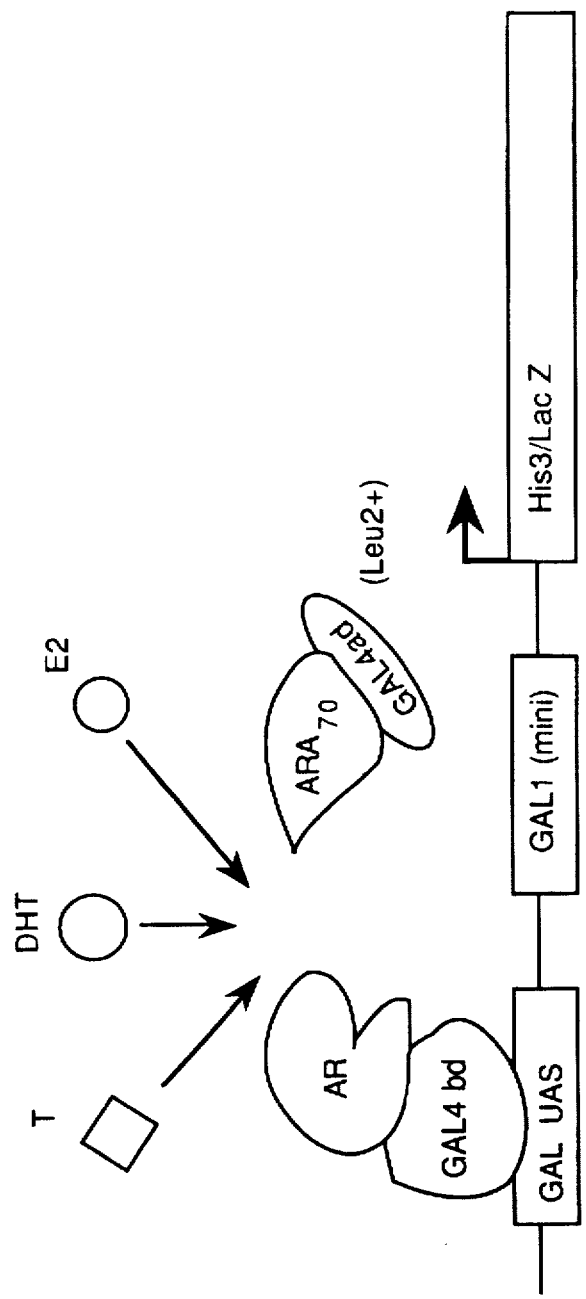
FIG. 1 is a schematic illustration of the use of the yeast two-hybrid system as used to identify $ARA_{70}$.

The present invention is enabled by a discovery of a new regulatory protein in humans. This regulatory protein is the androgen receptor associated protein, here designated $ARA_{70}$, which is a co-activator for the androgen receptor in human prostate cells. The $ARA_{70}$ factor is a ligand dependent protein that functions as a specific co-activator to enhance the transcriptional effect of androgen binding to the androgen receptor and also facilitates binding and activation of the androgen receptor by molecules previously not thought to have androgenic character.

Using a yeast two hybrid system, as described below, a cDNA encoding the $ARA_{70}$ molecule has been recovered from human brain cells. The recovered $ARA_{70}$ cDNA encodes a protein of 614 amino acids, with a calculated molecular weight of 70 kilodaltons. The full length cDNA has fully been sequenced, and the sequence is presented as SEQ ID NO 1 below. A search of the GenBank indicates that the $ARA_{70}$ cDNA shares a high degree of homology (99%) with a previously identified cDNA clone (RET-fused gene RFG), isolated from human thyroid as reported by Santoro et al., *Oncogene* 9, 509–516 (1994). Santoro et al. were unable to identify the main biological functions of the protein designated RFG, although the expression of the RFG in thyroid tumor suggests a potential role for the RFG molecule in thyroid carcinogenesis.

Northern Blot analysis indicated that the $ARA_{70}$ co-activator transcript is present in many tissues, including prostate, testis, adrenal gland, and thymus. Most human cell lines tested positive for the $ARA_{70}$ co-factor, with the significant exception of a human prostate cancer DU145 cell line, which did not express the $ARA_{70}$ molecule.

A specific ligand is necessary to actuate the co-activator role of $ARA_{70}$ as an enhancer of androgen receptor transcriptional activity. The most potent ligand yet identified is dihydrotestosterone (DHT). Using the yeast two hybrid model system, it has been demonstrated that the $ARA_{70}$ molecule will enhance the transcriptional activity of the androgen receptor near 10 fold, as measured in the presence of $10^{-10}M$ DHT. Furthermore, as described in greater detail below, the transcriptional activity of AR was activated by $ARA_{70}$ in the presence of $10^{-8}M$ 17β-estradiol (E2) in human prostate cells, but did not have the same enhancement of transcriptional activity in the presence of $10^{-6}M$ diethylstilbestrol (DES) an estrogen thought to be more potent. This data suggests that co-activators, such as $ARA_{70}$, for androgen receptor activity can mediate transcriptional activation of molecules previously thought to be essentially non-androgenic in a manner not previously detectable.

The availability of the $ARA_{70}$ cDNA clone described below enables the production of $ARA_{70}$ in foreign hosts. By joining the $ARA_{70}$ coding region to a promoter effective to initiate transcriptional activity in a desired host, whether eukaryotic or prokaryotic cells, quantities of $ARA_{70}$ can be manufactured in a foreign host for the uses described here and for other uses.

It is specifically envisioned that $ARA_{70}$ will have particular use as a constituent in a drug testing or screening protocol. It is a general practice in the evaluation of new clinical compounds for pharmaceutical utility that the compounds be tested for androgenic activity. Androgenic or antiandrogenic side effects can be important in the administration of some pharmaceutical agents. Previously, one of the methods used to test androgen activity was testing for binding and activation of the androgen receptor transcriptional activity. As the data herein suggests, the presence of $ARA_{70}$ in the presence of the androgen receptor greatly alters both the magnitude and the specificity of the transcriptional effect of the androgen receptor elicited by specific androgens. In addition, as evidenced with the estrogen E2 indicates, some molecules previously thought not to have androgenic activity will, in the presence of $ARA_{70}$, initiate transcriptional activity when bound to the androgen receptor and some molecules previously thought not to have inhibitory effect will limit or oppose the activity of the androgen receptor activated by $ARA_{70}$. Accordingly, in testing potential pharmaceutical molecules for androgenic or antiandrogenic effect, it would be important to include $ARA_{70}$ in the assay for androgenic/antiandrogenic activity to fully test androgenic effects actuated by the candidate molecule in vivo.

It is also anticipated that $ARA_{70}$ will serve as a clinical indicator of significant important for androgen related diseases. Significant androgen related diseases, such as prostate cancer, baldness, acne, and androgen insensitive syndromes, such as Tfm syndrome, may be due to defects in the co-activation mechanism between the androgen receptor and the $ARA_{70}$ molecule. Accordingly, it becomes a reasonable possibility, given the data presented herein, to assay the relative ratios of AR and $ARA_{70}$ in patients with such conditions. Such ratios may be measured by raising antibodies to both $ARA_{70}$ and to AR in performing quantitative methods to adjudge the relative quantity of the two molecules in a particular patient. Several methods exist for measuring such comparative ratios, including radio immunoassay, ELISA, immunostaining, or Western Blot. In addition, it would be possible to use the $ARA_{70}$ cDNA so as to construct probes for PCR assay for the presence of mutations of the normal DNA sequence in particular patients, or to generate transcript for Northern Blot assay or DNA for in situ hybridization assays.

The theory for such measurements of relative ratios AR to $ARA_{70}$ is that androgen insensitive related disease may be due to an imbalance between androgen receptor and androgen $ARA_{70}$ prevalence in target cells. Too much $ARA_{70}$ might over-sensitize the androgen receptor system, so as to be responsive to molecules not intended to have androgenic effect. Under sensitivity due to absence or non-function of $ARA_{70}$ may lead to androgen insensitivity at any levels. If too much $ARA_{70}$ was found to be present in a particular patient, that would suggest the use of down regulation mechanisms such as antisense or other similar mechanisms, in clinical system so as to reduce the levels of $ARA_{70}$ prevalent in a particular patient. If a particular patient had too little $ARA_{70}$, then it would be possible to deliver $ARA_{70}$ cDNA, protein, or DNA, into a patient by a variety of delivery mechanisms to increase levels of active $ARA_{70}$ in the patient.

In addition to testing potential pharmaceutical uses, the $ARA_{70}$ molecule would be useful for testing non-pharmaceutical compounds for potential androgenic/antiandrogenic activity. It is currently believed that many contaminants present within the environment at low samples have androgenic/antiandrogenic or estrogenic/antiestrogenic activity on various parts of the population. Since the $ARA_{70}$ increases androgen receptor specificity by over 10 fold, the sensitivity of androgen receptor tests can be greatly enhanced by the use of $ARA_{70}$ in such assay systems. As demonstrated by the fact that the addition of $ARA_{70}$ causes compounds classically thought to be only estrogenic, such as 17β estradiol, to exhibit androgenic activity, and by the fact that compounds thought to be only antiestrogenic, such as tamoxifen, can exhibit antiandrogenic activity, tests for androgenic/antiandrogenic activity would be incomplete without the use of $ARA_{70}$ as a co-factor in such reactions.

To test samples for androgenic/antiandrogenic activity, genetic constructions including expression cassettes for both the androgen receptor and $ARA_{70}$ would be transformed into host cells, such as a prostate cell line, in vitro. Also an easily detectable and quantifiable detector gene would be transformed in the cells as well. A suitable detector gene would be chloramphenicol acetyltransferase, or CAT, or luciferase the expression of which can be detected photometrically. The cells are then exposed to the pharmaceutical agent or environmental sample. Samples with androgenic/antiandrogenic activity will actuate increased or decreased detectable levels of CAT or luciferase activity.

EXAMPLES

Identification of the Androgen Receptor Specific-Associated Protein, $ARA_{70}$. To understand the mechanism of androgen-AR action, a yeast two-hybrid system, using the GAL4AR fusion protein as bait, was used to isolate a cDNA encoding $ARA_{70}$ which interacts specifically with AR. The fusion protein GAL4AR contains the GAL4 DNA binding domain (GAL4DBD) fused to the C-terminus of the androgen receptor. The fusion protein was used to screen for His-synthase gene positive clones from $3 \times 10^6$ transformants of the MATCHMAKER human brain library. Two of the initial 41 putatively positive clones clearly reacted with the AR fusion protein, by liquid assays performed by the method of Durfee et al. *Genes & Dev.* 7, 555–569 (1993).

In this yeast two-hybrid system, illustrated schematically in FIG. 1, yeast will survive when GAL4AR is co-expressed with $ARA_{70}$ in the presence of DHT. Neither GAL4AR nor $ARA_{70}$ was active when $ARA_{70}$ was expressed alone or when $ARA_{70}$ was co-expressed with GAL4RAR or GAL4TR4. Chang et al. *Proc. Natl. Acad. Sci. USA*, 91, 6040–6044 (1994), (GAL4 fusion proteins with two other members of the steroid receptor superfamily). These data, therefore, clearly suggest that $ARA_{70}$ can interact specifically with AR in the yeast cells.

We then tested whether the interaction of $ARA_{70}$ with AR in yeast was ligand-dependent. It was found that DHT ($5 \times 10^{-10}$M) can promote the interaction between $ARA_{70}$ and GAL4AR. Testosterone (T), a less potent androgen in the prostate, can also promote this interaction at higher concentrations ($5 \times 10^{-9}$M). Hydroxyflutamide (HF), an antiandrogen used in the treatment of prostate cancer, had no activity even at very high concentrations ($10^{-5}$M).

The RACE-PCR technique (10,11) was then used to clone the full-length $ARA_{70}$ cDNA, encoding a protein of 615 amino acids with a calculated molecular weight of 70K, (SEQ ID NO 1 & 2). A search of GenBank indicated that $ARA_{70}$ shares 99% homology (three different amino acids in the coding region) with one identified cDNA clone (RET-fused gene, RFG) isolated from human thyroid. Although the biological functions of RFG are mostly unknown, the expression of RFG in thyroid tumor may suggest some potential roles of RFG in thyroid carcinogenesis.

The Tissue Distribution of $ARA_{70}$. Northern blot analysis in mouse indicated that $ARA_{70}$ is expressed as an mRNA of ~3600 bp in many tissues, including prostate, testis, adrenal gland, and thymus. The relative expression of $ARA_{70}$ in the following mouse tissues, using adrenal gland as 100%, are: testis, 77%; prostate, 97%; preputial gland, 64%, thymus, 214%; submaxillary gland, 24%; muscle, 41%, heart, 73%; kidney, 37%; lung, 49%; fat pad, 20%; seminal vesicle and spleen undetectable. Among the cell lines (LNCaP, MCF-7, CHO, HeLa and DU145) tested, the human prostate cancer cell line, DU145, proved to be the only cell line that did not express $ARA_{70}$, and therefore was chosen for further functional study.

The In Vitro Interaction Between AR and $ARA_{70}$. To further confirm that the interaction that occurred in yeast cells is due to a direct interaction between AR and $ARA_{70}$, we applied an in vitro immunoprecipitation assay with an anti-AR antibody designated CW2. We demonstrated that CW2 can co-precipitate the AR and $ARA_{70}$ when in vitro transcribed/translated full-length human AR and $ARA_{70}$ were incubated with it in a lysate mixture. This precipitation is specific, as CW2 did not precipitate the $ARA_{70}$ in the absence of AR and CW2 did not precipitate two other proteins (RXR and TR4 orphan receptors) incubated with AR. A Far-Western assay also demonstrated that $ARA_{70}$ can bind to immobilized AR peptide containing DNA binding domain and hormone binding domain (AR-DBD/HBD), but not the BL21 protein lysate or the AR peptide containing the N-terminal and DNA binding domain of AR (AR-N/DBD). This data indicates that the association is due to a direct interaction between AR and $ARA_{70}$.

To perform the Far-Western assay, AR-N/DBD and AR-DBD/HBD were expressed, as polyhistidine fusion proteins by inserting the N-terminal or C-terminal fragments into pET 14b (Novagen). Proteins were separated on 10% polyacrylamide gel. $^{35}S$-labeled $ARA_{70}$ was diluted into hybridization buffer and the titers were hybridized overnight in the presence of 1 μM DHT. After three washings, filters were dried and autoradiographs made.

Stimulation of the Transcriptional Activity of AR by $ARA_{70}$. DU145 cells were co-transfected with $ARA_{70}$ and AR under the control of a eukaryotic promoter. Ligand-free AR was found to have minimal MMTV-ARE CAT reporter activity, with or without the presence of $ARA_{70}$. Addition of DHT resulted in a 6-fold increase of AR activity. This transcriptional activity was increased 58 (±3.2)-fold (mean±SEM; n=4) by the co-transfection of $ARA_{70}$ cDNAs in a dose-dependent manner. The induced activity reached a plateau at 4.5 μg of co-transfected $ARA_{70}$ cDNA. Additional $ARA_{70}$, beyond 4.5 μg, (up to 6 μg) did not affect the induced activity of AR in DU145 cells. To rule out any indirect effects on the basal activity of the MMTV-ARE CAT reporter, we removed the ARE DNA fragment from the reporter (MMTV-ΔARE-CAT). The results showed that $ARA_{70}$ induced no activity on this reporter in the presence or in the absence of DHT.

We also replaced $ARA_{70}$ with another nuclear orphan receptor-associated protein, TR4AP, in the AR: MMTV-ARE CAT reporter assay and found this protein had no effect in our assay. Furthermore, when we replaced DU145 cells with CHO cells, which express a relative abundance of $ARA_{70}$, we found that although the exogenously transfected $ARA_{70}$ did not show a dramatic effect on induction of AR transcriptional activity, the transfection of antisense $ARA_{70}$ did partially block the AR transcriptional activity. Together, these data strongly suggest that stimulation of AR transcriptional activity by $ARA_{70}$ occurs through a specific ligand-bound AR and the relative amount of AR vs $ARA_{70}$ in cells plays an important role for the activation of AR.

The effect of $ARA_{70}$ on transactivation of AR bound to different concentrations of testosterone (T), dihydrotestorenone (DHT) and hydroxy flutamide (HF) in DU145 cells was also tested. Whereas $10^{-10}M$ DHT maximized induced transcriptional activity of AR, with T a 10-fold higher concentration ($10^{-9}M$) was needed for maximum activity. HF induced very low at a pharmacological concentration ($10^{-6}M$). These results are consistent with the data generated from yeast cells and previous reports, which indicated DHT is more potent androgen in the prostate. In fact, the greater potency of DHT to modulate the interaction between AR and $ARA_{70}$ may actually provide the reason why DHT is a more potent androgen in prostate.

The enhancement of AR transcriptional activity from 6-fold to 58-fold by $ARA_{70}$ may explain androgen activity in the prostate that androgen-AR alone cannot explain. Since we detected $ARA_{70}$ in AR-positive LNCaP prostate cancer cells, but not in AR-negative DU145 cells, it will be important to determine if the expression of $ARA_{70}$ and its ability to interact properly with androgen-AR changes during the progression of prostate cancer from an androgen-dependent to an androgen-independent state.

$ARA_{70}$ Functions As a Specific Activator to Enhance the Transcriptional Activity of AR. We also examined the effect of $ARA_{70}$ on the transcriptional activity of several other steroid receptors through their cognate DNA response elements. While $ARA_{70}$ induces the transcriptional activity of AR up to 10-fold, $ARA_{70}$ can only slightly enhance (up to 2-fold) the transcription activity of other steroid receptors, such as GR, PR, and ER. These results clearly indicate that $ARA_7$. is a very specific co-activator for AR.

Several proteins have been demonstrated to interact with other steroid receptors in a ligand-dependent or ligand-independent manner. However, none of these proteins have been shown to enhance specifically AR-mediated transcriptional activity; therefore, it is likely that $ARA_{70}$ has a different mechanism for interacting with AR.

In summary, our data demonstrated that $ARA_{70}$ is the first identified ligand-dependent associated protein for AR which may function as a specific co-activator for inducing the transcriptional activity of AR in human prostate cells. Further studying the potential role of $ARA_{70}$ may therefore help us to understand better the molecular mechanism of androgen action.

Transcriptional Activity of AR Induced by 17β-estradiol

Tests in both DU145 cells and yeast cells demonstrated that 17β-estradiol, at a concentration of $10^{-8}M$ or higher, stimulated the transcriptional activity of AR in the presence of $ARA_{70}$. By contrast, diethylstilbestrol (DES), even at concentrations of $10^{-6}M$, did not increase AR transcriptional activity. This result may explain why DES, but not 17β-estradiol, has fewer side effects when used by clinicians to treat prostate cancer patients.

Antiandrogenic Activity of Tamoxifen and $ICI_{162780}$

Similar protocols were repeated but, instead of adding an androgen or estrogen, tamoxifen and $ICI_{162780}$ were added, both compounds known to be antiestrogenic. The data revealed that both compounds inhibited AR initiated transcriptional activity in human prostate cells. This demonstrates the ability to assay for antiandrogenic effects using this same style of assay.

We claim:

1. A constructed DNA molecule comprising 5' to 3' a promoter effective in a host cell to cause expression of a protein coding region;

a protein coding region for human ARA$_{70}$ protein; and the promoter and the protein coding region not natively associated with each other.

2. A eukaryotic host cell hosting the DNA sequence of claim 1.

3. An isolated DNA molecule apart from a host having the sequence of SEQ ID NO. 1.

4. A constructed DNA molecule comprising 5' to 3' a promoter effective in a host cell to cause expression of a protein coding region;

a protein coding region coding for a protein having the sequence of SEQ ID NO 2.; and the promoter and the protein coding region not natively associated with each other.

5. A eukaryotic host cell hosting the DNA sequence of claim 4.

6. A method for testing the androgenic or antiandrogenic effect of a chemical compound in vitro comprising the steps of transforming host cells with a genetic construction effective in that host cell to produce both human androgen receptor protein and $ARA_{70}$ protein;

exposing the transformed host cells to the chemical compound; and measuring the level of transcriptional activity caused by the androgen receptor.

7. The method of claim 6 wherein the host cells are prostate cells.

8. The method of claim 6 wherein the genetic construction producing the $ARA_{70}$ protein has the DNA sequence of SEQ ID NO. 1.

9. The method of claim 6 wherein the genetic construction also includes a reporter gene, the expression of which can be detected and quantified.

10. The method of claim 6 wherein the chemical compound is a pharmaceutical.

11. The method of claim 6 wherein the chemical compound is contained in an environmental sample.

12. The method of claim 9 wherein the reporter gene is the chloramphenicol acetyltransferase gene.

* * * * *

UNITED STATES PATENT AND TRADEMARK OFFICE
CERTIFICATE OF CORRECTION

PATENT NO.  : 5,789,170
DATED       : August 4, 1998
INVENTOR(S) : Chawnshang Chang, et. al.

It is certified that error appears in the above-identified patent and that said Letters Patent is hereby corrected as shown below:

Title page, item [54] after the Title, insert
--This invention was made with United States government support awarded by NIH, Grant No. DK51346. The United States Government has certain rights in this invention.--

Signed and Sealed this

Seventeenth Day of November, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1845 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1845

( x i ) SEQUENCE DESCRIPTION: SEQ ID NO:1:

```
ATG AAT ACC TTC CAA GAC CAG AGT GGC AGC TCC AGT AAT AGA GAA CCC        48
Met Asn Thr Phe Gln Asp Gln Ser Gly Ser Ser Ser Asn Arg Glu Pro
 1               5                  10                  15

CTT TTG AGG TGT AGT GAT GCA CGG AGG GAC TTG GAG CTT GCT ATT GGT        96
Leu Leu Arg Cys Ser Asp Ala Arg Arg Asp Leu Glu Leu Ala Ile Gly
             20                  25                  30

GGA GTT CTC CGG GCT GAA CAG CAA ATT AAA GAT AAC TTG CGA GAG GTC       144
Gly Val Leu Arg Ala Glu Gln Gln Ile Lys Asp Asn Leu Arg Glu Val
         35                  40                  45

AAA GCT CAG ATT CAC AGT TGC ATA AGC CGT CAC CTG GAA TGT CTT AGA       192
Lys Ala Gln Ile His Ser Cys Ile Ser Arg His Leu Glu Cys Leu Arg
 50                  55                  60

AGC CGT GAG GTA TGG CTG TAT GAA CAG GTG GAC CTT ATT TAT CAG CTT       240
Ser Arg Glu Val Trp Leu Tyr Glu Gln Val Asp Leu Ile Tyr Gln Leu
 65                  70                  75                  80

AAA GAG GAG ACA CTT CAA CAG CAG GCT CAG CAG CTC TAC TCG TTA TTG       288
Lys Glu Glu Thr Leu Gln Gln Gln Ala Gln Gln Leu Tyr Ser Leu Leu
             85                  90                  95

GGC CAG TTC AAT TGT CTT ACT CAT CAA CTG GAG TGT ACC CAA AAC AAA       336
Gly Gln Phe Asn Cys Leu Thr His Gln Leu Glu Cys Thr Gln Asn Lys
            100                 105                 110

GAT CTA GCC AAT CAA GTC TCT GTG TGC CTG GAG AGA CTG GGC AGT TTG       384
Asp Leu Ala Asn Gln Val Ser Val Cys Leu Glu Arg Leu Gly Ser Leu
        115                 120                 125

ACC CTT AAG CCT GAA GAT TCA ACT GTC CTG CTC TTT GAA GCT GAC ACA       432
Thr Leu Lys Pro Glu Asp Ser Thr Val Leu Leu Phe Glu Ala Asp Thr
    130                 135                 140

ATT ACT CTG CGC CAG ACC ATC ACC ACA TTT GGG TCT CTC AAA ACC ATT       480
Ile Thr Leu Arg Gln Thr Ile Thr Thr Phe Gly Ser Leu Lys Thr Ile
145                 150                 155                 160

CAA ATT CCT GAG CAC TTG ATG GCT CAT GCT AGT TCA GCA AAT ATT GGG       528
Gln Ile Pro Glu His Leu Met Ala His Ala Ser Ser Ala Asn Ile Gly
                165                 170                 175

CCC TTC CTG GAG AAG AGA GGC TGT ATC TCC ATG CCA GAG CAG AAG TCA       576
Pro Phe Leu Glu Lys Arg Gly Cys Ile Ser Met Pro Glu Gln Lys Ser
            180                 185                 190

GCA TCC GGT ATT GTA GCT GTC CCT TTC AGC GAA TGG CTC CTT GGA AGC       624
Ala Ser Gly Ile Val Ala Val Pro Phe Ser Glu Trp Leu Leu Gly Ser
        195                 200                 205

AAA CCT GCC AGT GGT TAT CAA GCT CCT TAC ATA CCC AGC ACC GAC CCC       672
Lys Pro Ala Ser Gly Tyr Gln Ala Pro Tyr Ile Pro Ser Thr Asp Pro
    210                 215                 220
```

```
CAG GAC TGG CTT ACC CAA AAG CAG ACC TTG GAG AAC AGT CAG ACT TCT        720
Gln Asp Trp Leu Thr Gln Lys Gln Thr Leu Glu Asn Ser Gln Thr Ser
225             230             235             240

TCC AGA GCC TGC AAT TTC TTC AAT AAT GTC GGG GGA AAC CTA AAG GGC        768
Ser Arg Ala Cys Asn Phe Phe Asn Asn Val Gly Gly Asn Leu Lys Gly
                245             250             255

TTA GAA AAC TGG CTC CTC AAG AGT GAA AAA TCA AGT TAT CAA AAG TGT        816
Leu Glu Asn Trp Leu Leu Lys Ser Glu Lys Ser Ser Tyr Gln Lys Cys
            260             265             270

AAC AGC CAT TCC ACT ACT AGT TCT TTC TCC ATT GAA ATG GAA AAG GTT        864
Asn Ser His Ser Thr Thr Ser Ser Phe Ser Ile Glu Met Glu Lys Val
        275             280             285

GGA GAT CAA GAG CTT CCT GAT CAA GAT GAG ATG GAC CTA TCA GAT TGG        912
Gly Asp Gln Glu Leu Pro Asp Gln Asp Glu Met Asp Leu Ser Asp Trp
    290             295             300

CTA GTG ACT CCC CAG GAA TCC CAT AAG CTG CGG AAG CCT GAG AAT GGC        960
Leu Val Thr Pro Gln Glu Ser His Lys Leu Arg Lys Pro Glu Asn Gly
305             310             315             320

AGT CGT GAA ACC AGT GAG AAG TTT AAG CTC TTA TTC CAG TCC TAT AAT       1008
Ser Arg Glu Thr Ser Glu Lys Phe Lys Leu Leu Phe Gln Ser Tyr Asn
                325             330             335

GTG AAT GAT TGG CTT GTC AAG ACT GAC TCC TGT ACC AAC TGT CAG GGA       1056
Val Asn Asp Trp Leu Val Lys Thr Asp Ser Cys Thr Asn Cys Gln Gly
            340             345             350

AAC CAG CCC AAA GGT GTG GAG ATT GAA AAC CTG GGC AAT CTG AAG TGC       1104
Asn Gln Pro Lys Gly Val Glu Ile Glu Asn Leu Gly Asn Leu Lys Cys
        355             360             365

CTG AAT GAC CAC TTG GAG GCC AAG AAA CCA TTG TCC ACC CCC AGC ATG       1152
Leu Asn Asp His Leu Glu Ala Lys Lys Pro Leu Ser Thr Pro Ser Met
    370             375             380

GTT ACA GAG GAT TGG CTT GTC CAG AAC CAT CAG GAC CCA TGT AAG GTA       1200
Val Thr Glu Asp Trp Leu Val Gln Asn His Gln Asp Pro Cys Lys Val
385             390             395             400

GAG GAG GTG TGC AGA GCC AAT GAG CCC TGC ACA AGC TTT GCA GAG TGT       1248
Glu Glu Val Cys Arg Ala Asn Glu Pro Cys Thr Ser Phe Ala Glu Cys
                405             410             415

GTG TGT GAT GAG AAT TGT GAG AAG GAG GCT CTG TAT AAG TGG CTT CTG       1296
Val Cys Asp Glu Asn Cys Glu Lys Glu Ala Leu Tyr Lys Trp Leu Leu
            420             425             430

AAG AAA GAA GGA AAG GAT AAA AAT GGG ATG CCT GTG GAA CCC AAA CCT       1344
Lys Lys Glu Gly Lys Asp Lys Asn Gly Met Pro Val Glu Pro Lys Pro
        435             440             445

GAG CCT GAG AAG CAT AAA GAT TCC CTG AAT ATG TGG CTC TGT CCT AGA       1392
Glu Pro Glu Lys His Lys Asp Ser Leu Asn Met Trp Leu Cys Pro Arg
    450             455             460

AAA GAA GTA ATA GAA CAA ACT AAA GCA CCA AAG GCA ATG ACT CCT TCT       1440
Lys Glu Val Ile Glu Gln Thr Lys Ala Pro Lys Ala Met Thr Pro Ser
465             470             475             480

AGA ATT GCT GAT TCC TTC CAA GTC ATA AAG AAC AGC CCC TTG TCG GAG       1488
Arg Ile Ala Asp Ser Phe Gln Val Ile Lys Asn Ser Pro Leu Ser Glu
                485             490             495

TGG CTT ATC AGG CCC CCA TAC AAA GAA GGA AGT CCC AAG GAA GTG CCT       1536
Trp Leu Ile Arg Pro Pro Tyr Lys Glu Gly Ser Pro Lys Glu Val Pro
            500             505             510

GGT ACT GAA GAC AGA GCT GGC AAA CAG AAG TTT AAA AGC CCC ATG AAT       1584
Gly Thr Glu Asp Arg Ala Gly Lys Gln Lys Phe Lys Ser Pro Met Asn
        515             520             525

ACT TCC TGG TGT TCC TTT AAC ACA GCT GAC TGG GTC CTG CCA GGA AAG       1632
Thr Ser Trp Cys Ser Phe Asn Thr Ala Asp Trp Val Leu Pro Gly Lys
    530             535             540
```

-continued

| | | | | | | | | | | | | | | | | |
|---|---|---|---|---|---|---|---|---|---|---|---|---|---|---|---|---|
| AAG | ATG | GGC | AAC | CTC | AGC | CAG | TTA | TCT | TCT | GGA | GAA | GAC | AAG | TGG | CTG | 1680 |
| Lys | Met | Gly | Asn | Leu | Ser | Gln | Leu | Ser | Ser | Gly | Glu | Asp | Lys | Trp | Leu | |
| 545 | | | | 550 | | | | | 555 | | | | | 560 | | |
| CTT | CGA | AAG | AAG | GCC | CAG | GAA | GTA | TTA | CTT | AAT | TCA | CCT | CTA | CAG | GAG | 1728 |
| Leu | Arg | Lys | Lys | Ala | Gln | Glu | Val | Leu | Leu | Asn | Ser | Pro | Leu | Gln | Glu | |
| | | | | 565 | | | | | 570 | | | | | 575 | | |
| GAA | CAT | AAC | TCC | CCC | CCA | GAC | CAT | TAT | GGC | CTC | CCT | GCA | GTT | TGT | GAT | 1776 |
| Glu | His | Asn | Ser | Pro | Pro | Asp | His | Tyr | Gly | Leu | Pro | Ala | Val | Cys | Asp | |
| | | | 580 | | | | | 585 | | | | | 590 | | | |
| CTC | TTT | TCC | TGT | ATG | CAG | CTT | AAA | GTT | GAT | AAA | GAG | AAG | TGG | TTA | TAT | 1824 |
| Leu | Phe | Ser | Cys | Met | Gln | Leu | Lys | Val | Asp | Lys | Glu | Lys | Trp | Leu | Tyr | |
| | | 595 | | | | | 600 | | | | | 605 | | | | |
| CAG | ACT | CCT | CTA | CAG | ATG | TGA | | | | | | | | | | 1845 |
| Gln | Thr | Pro | Leu | Gln | Met | * | | | | | | | | | | |
| 610 | | | | | 615 | | | | | | | | | | | |

( 2 ) INFORMATION FOR SEQ ID NO:2:

( i ) SEQUENCE CHARACTERISTICS:
      ( A ) LENGTH: 614 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Asn | Thr | Phe | Gln | Asp | Gln | Ser | Gly | Ser | Ser | Ser | Asn | Arg | Glu | Pro |
| 1 | | | | 5 | | | | | 10 | | | | | 15 | |
| Leu | Leu | Arg | Cys | Ser | Asp | Ala | Arg | Arg | Asp | Leu | Glu | Leu | Ala | Ile | Gly |
| | | | 20 | | | | | 25 | | | | | 30 | | |
| Gly | Val | Leu | Arg | Ala | Glu | Gln | Gln | Ile | Lys | Asp | Asn | Leu | Arg | Glu | Val |
| | | | 35 | | | | | 40 | | | | | 45 | | |
| Lys | Ala | Gln | Ile | His | Ser | Cys | Ile | Ser | Arg | His | Leu | Glu | Cys | Leu | Arg |
| | 50 | | | | | 55 | | | | | 60 | | | | |
| Ser | Arg | Glu | Val | Trp | Leu | Tyr | Glu | Gln | Val | Asp | Leu | Ile | Tyr | Gln | Leu |
| 65 | | | | | 70 | | | | | 75 | | | | | 80 |
| Lys | Glu | Glu | Thr | Leu | Gln | Gln | Gln | Ala | Gln | Gln | Leu | Tyr | Ser | Leu | Leu |
| | | | | 85 | | | | | 90 | | | | | 95 | |
| Gly | Gln | Phe | Asn | Cys | Leu | Thr | His | Gln | Leu | Glu | Cys | Thr | Gln | Asn | Lys |
| | | | | 100 | | | | | 105 | | | | | 110 | |
| Asp | Leu | Ala | Asn | Gln | Val | Ser | Val | Cys | Leu | Glu | Arg | Leu | Gly | Ser | Leu |
| | | | 115 | | | | | 120 | | | | | 125 | | |
| Thr | Leu | Lys | Pro | Glu | Asp | Ser | Thr | Val | Leu | Leu | Phe | Glu | Ala | Asp | Thr |
| | | | 130 | | | | | 135 | | | | | 140 | | |
| Ile | Thr | Leu | Arg | Gln | Thr | Ile | Thr | Thr | Phe | Gly | Ser | Leu | Lys | Thr | Ile |
| 145 | | | | | 150 | | | | | 155 | | | | | 160 |
| Gln | Ile | Pro | Glu | His | Leu | Met | Ala | His | Ala | Ser | Ser | Ala | Asn | Ile | Gly |
| | | | | 165 | | | | | 170 | | | | | 175 | |
| Pro | Phe | Leu | Glu | Lys | Arg | Gly | Cys | Ile | Ser | Met | Pro | Glu | Gln | Lys | Ser |
| | | | 180 | | | | | 185 | | | | | 190 | | |
| Ala | Ser | Gly | Ile | Val | Ala | Val | Pro | Phe | Ser | Glu | Trp | Leu | Leu | Gly | Ser |
| | | | 195 | | | | | 200 | | | | | 205 | | |
| Lys | Pro | Ala | Ser | Gly | Tyr | Gln | Ala | Pro | Tyr | Ile | Pro | Ser | Thr | Asp | Pro |
| | | | 210 | | | | | 215 | | | | | 220 | | |
| Gln | Asp | Trp | Leu | Thr | Gln | Lys | Gln | Thr | Leu | Glu | Asn | Ser | Gln | Thr | Ser |
| 225 | | | | | 230 | | | | | 235 | | | | | 240 |
| Ser | Arg | Ala | Cys | Asn | Phe | Phe | Asn | Asn | Val | Gly | Gly | Asn | Leu | Lys | Gly |
| | | | | 245 | | | | | 250 | | | | | 255 | |

```
Leu Glu Asn Trp Leu Leu Lys Ser Glu Lys Ser Ser Tyr Gln Lys Cys
            260             265             270

Asn Ser His Ser Thr Thr Ser Ser Phe Ser Ile Glu Met Glu Lys Val
        275             280             285

Gly Asp Gln Glu Leu Pro Asp Gln Asp Glu Met Asp Leu Ser Asp Trp
    290             295             300

Leu Val Thr Pro Gln Glu Ser His Lys Leu Arg Lys Pro Glu Asn Gly
305             310             315             320

Ser Arg Glu Thr Ser Glu Lys Phe Lys Leu Leu Phe Gln Ser Tyr Asn
            325             330             335

Val Asn Asp Trp Leu Val Lys Thr Asp Ser Cys Thr Asn Cys Gln Gly
            340             345             350

Asn Gln Pro Lys Gly Val Glu Ile Glu Asn Leu Gly Asn Leu Lys Cys
        355             360             365

Leu Asn Asp His Leu Glu Ala Lys Lys Pro Leu Ser Thr Pro Ser Met
    370             375             380

Val Thr Glu Asp Trp Leu Val Gln Asn His Gln Asp Pro Cys Lys Val
385             390             395             400

Glu Glu Val Cys Arg Ala Asn Glu Pro Cys Thr Ser Phe Ala Glu Cys
            405             410             415

Val Cys Asp Glu Asn Cys Glu Lys Glu Ala Leu Tyr Lys Trp Leu Leu
            420             425             430

Lys Lys Glu Gly Lys Asp Lys Asn Gly Met Pro Val Glu Pro Lys Pro
        435             440             445

Glu Pro Glu Lys His Lys Asp Ser Leu Asn Met Trp Leu Cys Pro Arg
    450             455             460

Lys Glu Val Ile Glu Gln Thr Lys Ala Pro Lys Ala Met Thr Pro Ser
465             470             475             480

Arg Ile Ala Asp Ser Phe Gln Val Ile Lys Asn Ser Pro Leu Ser Glu
            485             490             495

Trp Leu Ile Arg Pro Pro Tyr Lys Glu Gly Ser Pro Lys Glu Val Pro
        500             505             510

Gly Thr Glu Asp Arg Ala Gly Lys Gln Lys Phe Lys Ser Pro Met Asn
    515             520             525

Thr Ser Trp Cys Ser Phe Asn Thr Ala Asp Trp Val Leu Pro Gly Lys
    530             535             540

Lys Met Gly Asn Leu Ser Gln Leu Ser Ser Gly Glu Asp Lys Trp Leu
545             550             555             560

Leu Arg Lys Lys Ala Gln Glu Val Leu Leu Asn Ser Pro Leu Gln Glu
            565             570             575

Glu His Asn Ser Pro Pro Asp His Tyr Gly Leu Pro Ala Val Cys Asp
        580             585             590

Leu Phe Ser Cys Met Gln Leu Lys Val Asp Lys Glu Lys Trp Leu Tyr
        595             600             605

Gln Thr Pro Leu Gln Met  *
610             615
```